(12) United States Patent
Speck (10) Patent No.: US 6,319,703 B1
(45) Date of Patent: *Nov. 20, 2001

(54) RECOMBINANT VIRUS VECTORS

(76) Inventor: Peter G. Speck, 535 N. Michigan Ave., #812, Chicago, IL (US) 60611

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/776,497

(22) PCT Filed: Jul. 28, 1995

(86) PCT No.: PCT/GB95/01790

§ 371 Date: Apr. 25, 1997

§ 102(e) Date: Apr. 25, 1997

(87) PCT Pub. No.: WO96/04395

PCT Pub. Date: Feb. 15, 1996

(30) Foreign Application Priority Data

Jul. 29, 1994 (GB) .................................................. 9415369

(51) Int. Cl.⁷ .............................. C12N 7/00; C12N 7/01; C12N 7/04; C12N 15/869
(52) U.S. Cl. ................... 435/235.1; 435/236; 424/199.1; 424/229.1; 424/231.1; 424/93.2; 424/205.1
(58) Field of Search .................. 424/199.1, 205.1, 424/229.1, 230.1, 231.1, 93.2; 435/69.1, 235.1, 236, 320.1

(56) References Cited

U.S. PATENT DOCUMENTS

| | | | |
|---|---|---|---|
| 5,626,850 | * 5/1997 | Visser et al. | 424/199.1 |
| 5,658,724 | 8/1997 | DeLuca | 435/5 |
| 5,804,413 | 9/1998 | DeLuca | 435/69.1 |
| 5,879,934 | 3/1999 | DeLuca | 435/320.1 |
| 6,086,902 | * 7/2000 | Zamb et al. | 424/299.1 |

FOREIGN PATENT DOCUMENTS

| | | | |
|---|---|---|---|
| 91/02788 | 3/1991 | (WO) . | |
| 94/03207 | 2/1994 | (WO) . | |
| 92/05263 | * 4/1992 | (WO) | C12N/15/86 |

OTHER PUBLICATIONS

Glorioso et al. (Journal of Cellular Biochemistry, Supplement 18A, p. 219, Jan. 1994).
Roizman et al. (Fundamental Virology, Second Edition, ed. B.N.Fields et al., Raven Press, NY, pp. 849–895), 1991.
Poffenberger et al. (Arch. Virol. 139: 111–119, 1994).
Nguyen, L.H. et al. Journal of Virollogy 66: 7067–7072, Dec. 1992.*
Verma, I.M. et al. nature 389:239–242, Sep. 1997.*
Orkin, S. H. et al. Report and recommendations of the panel to assess the NIH investment in research on gene therapy, Dec. 1995.*

* cited by examiner

Primary Examiner—Mary E. Mosher
(74) Attorney, Agent, or Firm—Klarquist Sparkman, LLP (57) ABSTRACT

A mutant herpesvirus that can be used a recombinant virus vector includes (a) a mutation such that the mutant virus has a reduced ability in comparison with a parent type to cause lysis of an infected cell, and (b) an inactivating mutation in a gene essential for the production of infectious virus. An example is a HSV1 mutant lacking the essential glycoprotein gH gene and having a mutation impairing the function of the gene product VP16. A heterologous gene can be carried at the site of the inactivated essential gene, e.g. a gene suitable for administering gene therapy. The vector has an increased margin of safety over known herpesvirus vectors in respect of incidence of cytopathic effects and/or risk of infection.

9 Claims, 3 Drawing Sheets

Fig. 1.

OLIGONUCLEOTIDES USED.

MB62  TCAAAGCTTCTGCAGGGCGGCGGGTCGTGG

MB63  TCAGTTAACGGACCCCGTCCCTAACCCACG

MB61  TCAGTTAACAGCCCCTCTTTGCTTTCCCTC

MB58  TCAGAATTCGAGCAGCTCCTCATGTTCGAC

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      oligonucleotide MB62

<400> SEQUENCE: 1
tcaaagcttc tgcagggcgg cgggtcgtgg                                       30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      oligonucleotide MB63

<400> SEQUENCE: 2
tcagttaacg gaccccgtcc ctaacccacg                                       30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      oligonucleotide MB61

<400> SEQUENCE: 3
tcagttaaca gcccctcttt gctttccctc                                       30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      oligonucleotide MB58

<400> SEQUENCE: 4
tcagaattcg agcagctcct catgttcgac                                       30

RECOMBINANT VIRUS VECTORS

FIELD OF THE INVENTION

The present invention relates to mutant viruses that can be used as recombinant virus vectors. The invention also relates to mutant virus vectors that can be used for the delivery to cells of nucleotide sequence(s) encoding polypeptide(s). The invention also relates to cells infected by such mutant viruses and to materials and methods for delivering nucleotide sequence(s) encoding polypeptide(s) to host cells ex vivo or to treated subjects in vivo such as human patients by use of a recombinant virus vector based on such mutant herpesvirus.

BACKGROUND OF THE INVENTION

Many disorders which manifest in symptoms such as respiratory distress, growth abnormalities, muscular insufficiency, and/or mental retardation result from the inheritance of genetic material which is defective in that a gene coding for the synthesis of a protein is either completely or partially absent or of an incorrect coding sequence. Thus the defect results in the disruption of the normal activities of cells which are dependent upon the normal protein for correct functioning.

The affected protein can be for example an enzyme, a storage protein, a transport protein, a hormone, a recognition protein such as a cell surface receptor or a cell pore protein.

Typical examples of disorders of this type are cystic fibrosis, Tay-Sachs disease. B-thalassaemia and Hurler disease.

If the particular genetic defect can be identified, there is the possibility that it can be correctable by providing the patient with a correct version of the gene.

Herpes simplex virus (HSV) has been considered to have potential as a vector for such gene therapy, because it has the potential to carry large inserts of foreign DNA and because it is capable of existing as a latent, quiescent genetic element in cells (particularly neurones) for the lifetime of the host. Nevertheless, a disadvantage of wild-type HSV is that it is a lytic virus whose growth results in cell damage or cell death. Therefore, the use of an unmodified form of an HSV virus vector is unacceptable, and even some modified forms can carry significant risks.

The construction and characterization of a HSV-1 mutant (in1814) unable to transinduce immediate early gene expression, and essentially avirulent when injected into mice is described by C I Ace et al. J Virol 63(5) 1989 pp 2260–2269, and specification WO 91/02788 (C M Preston & C I Ace: University of Glasgow) describes HSV1 mutants including in1814 capable of establishing latent infection in a neuronal host cell and of causing expression of an inserted therapeutic gene.

In mutants such as in1814 the gene for VP16 is modified: VP16 is a structural component of the virus particle which acts as a transcriptional activator of immediate-early genes of the infecting genome. This mutant enters cells normally. although it has a reduced ability to enter the productive lytic cycle.

SUMMARY AND DESCRIPTION OF THE INVENTION

The present inventor considers that although the mutants of the prior art include an essentially avirulent (in mice) mutant such as in1814, it remains desirable to provide a further genetic defect in a virus to be used as a vector for gene therapy and for other purposes.

The present invention provides mutant herpesvirus which (a) carries a mutation such that it has a reduced ability to enter the productive lytic cycle in an infected cell or cause lysis of an infected cell, and (b) has a genome which is defective in respect of a gene essential for the production of infectious virus; the invention also provides methods for its production and its uses. The mutant herpesvirus genome thus carries (a) a mutation such that the mutant virus has a reduced ability in comparison with a parent type to cause lysis of an infected cell, and (b) an inactivating mutation in a gene essential for the production of infectious virus.

The further genetic defect in the form of inactivating mutation (b) brings a safety advantage in that this mutation can be such that it is not susceptible of complementation within the host cell, and is practically free from risk of reversion. Such a further genetic defect is known per se, being of the kind described in specification WO 92/05263 (S C Inglis et al: Immunology Ltd) and corresponding GB 2 263 480 (Cantab Pharmaceuticals Ltd) entitled "Viral Defective Vaccine Produced by Transcomplementing Cell Line" which describe a mutant virus for use as a vaccine, having a genome which is defective in respect of a gene essential for the production of normal infectious virus. Mutant virus of this kind can be propagated on a recombinant complementing cell which provides the virus with the product of the deleted gene, thus making it possible to grow the virus in tissue culture.

A mutant herpesvirus of the present invention can be used for example as a vector for a gene, heterologous to the virus itself, to be administered to and expressed in cells of a treated subject by way of gene therapy.

Embodiments of the invention can in this connection have an advantage in that they can combine an increased margin of safety over known herpesvirus vectors in respect of the incidence of cytopathic effects and/or of the risk of reversion to virulence, along with useful persistence of expression. in cells of the treated subject, of the gene carried by the vector.

The mutant herpesvirus can also be used as a vector for a gene encoding an antigen against which an immune response is desired in the treated subject.

The mutant herpesvirus can be a mutant of any herpesvirus e.g. a mutant of a mammalian herpesvirus, e.g. a human herpesvirus. Examples of herpesviruses of which mutants are provided according to embodiments of the invention include herpes simplex virus of type 1 (HSV-1) or type 2 (HSV-2). a human or animal cytomegalovirus (CMV). e.g. human cytomegalovirus (HCMV), varicella zoster virus (VZV), Epstein-Barr virus (EBV), and human herpesvirus 6 and 7. Animal viruses of which mutants are provided according to embodiments of the invention include pseudorabies virus (PRV), equine and bovine herpesvirus including EHV and BHV types such as IBRV, and Marek's disease virus (MDV) and related viruses. The nomenclature of the genes of herpesviruses and their many corresponding homologues is diverse and where the context admits. mention of a gene in connection with a herpesvirus includes reference, in connection with other herpesviruses possessing a homologue of that gene, to the corresponding homologue.

A mutant herpesvirus of the invention carries at least one mutation that reduces its ability to cause lysis of an infected cell. Where for example the herpes virus is HSV-1, the defect in the genome which reduces the mutant's ability to enter a productive lytic cycle as compared to wild-type virus can for example comprise a mutation in the VP16 gene.

A preferred example of such a mutation is a mutation in the gene corresponding to VP16 (otherwise designated Vmw65 or alpha-TIF) in herpes simplex virus type 1, which is effective to reduce (by comparison with a parent type), or substantially remove the transinducing properties of the protein encoded by that gene, especially while retaining its structural role. A particular example of such a mutation is the in1814 mutation in HSV1. Further examples of such mutations include VP16 mutations such as a transition or transversion alteration of 1 to 72 base pairs, an oligonucleotide insert of 3 to 72 base pairs, or a deletion of 3 to 72 base pairs, e.g. at a position within the region corresponding to aminoacids 289 and 412 of the HSV1 VP16 protein, as described in specification WO 91/02788, hereby incorporated by reference, or other mutations in the gene corresponding to VP16 that allow growth of the mutant virus in cell culture in the presence of hexamethylene bisacetamide (HMBA).

Thus the present invention also provides a mutant herpesvirus e.g.

HSV-1 which comprises a genome which (i) has a defect such that in comparison to the wild-type form of the herpesvirus, or other corresponding parent strain in relation to the mutation, the mutant has a reduced ability to cause lysis of an infected cell or enter a productive lytic cycle, e.g. such a mutation in the VP16 gene as is mentioned herein: (ii) has an inactivating defect in a gene essential for the production of infectious virus (e.g. an essential viral glycoprotein gene such as for example the gH gene). The mutant viral genome can include (iii) a site for the insertion of a coding sequence(s) for one or more polypeptides.

Although the VP16 gene (along with for example the gH gene) has been specifically mentioned so far as a suitable gene for mutation in order to make a mutant virus as described. alternative genes can be rendered defective so that as compared to wild-type, the resultant mutant virus has a reduced ability to enter a productive lytic cycle or otherwise cause lysis of the infected cell.

Thus, further examples of the mutant viruses of the invention can 25 be based on a mutation in a herpesvirus immediate early gene, e.g. corresponding to ICPO, ICP4, ICP22 and ICP27. Such a mutation in at least one immediate early gene can be a mutation that impairs the expression of the gene or the function of the gene product so that the resulting mutant has a reduced ability to cause lysis of an infected cell. Thus. a useful such mutation is effective to reduce the ability of the virus to-cause expression of at least one immediate early gene function. It is considered that such mutations can hinder the ability of the virus to enter a productive lytic cycle in the infected cell. Alternatively, the mutation can involve complete inactivation, possibly complete deletion, of the gene concerned (e.g. in the case of duplicated viral genes such as ICP4, a deletion in both copies). In connection with the abovementioned genes of HSV1 reference is made to D J McGeoch. J gen Virol 69 (1988) 1531–1574: D J McGeoch et al. Nucl Acids Res 14 (1986) 1727–1745: and to D J McGeoch et al, J mol Biol 181 (1985) 1–13, and 40. references cited therein, as well as to D J McGeoch, 'The Genomes of the Human Herpesviruses', in Ann Rev Microbiol 43 (1989) pp 235–265, for data and references given therein. In relation to genes of further herpesviruses reference is further made to data published for example in respect of Epstein-Barr virus EBV (R Baer et al. in Nature 310 (1984) 207–211). human cytomegalovirus CMV (Weston and Barrell in J Mol Biol 192 (1986) 177–208). varicella zoster virus VZV (A J Davison et al. in J Gen Virol 67 (1986) 759–816).

In addition to the mutation (a) described above, the mutant herpesvirus provided by the invention also carries at least a further mutation. This is an inactivating mutation in at least one essential viral gene, this inactivating mutation being such that although the mutant virus can cause production of infectious progeny virus particles when it is grown on cells of a complementing cell line made recombinant so that the cell line can express a gene function corresponding to the function of the essential gene that was inactivated in the viral genome, nevertheless the mutant virus is unable to cause production of infectious progeny virus particles when it infects a cell other than a cell of such a recombinant cell line. e.g. when the mutant virus infects a normal (non-recombinant) host cell not containing a viral gene corresponding to the inactivating mutation. Examples of such mutations in essential viral genes are described for example in specifications WO 92/05263 (Inglis et al: Immunology Ltd), WO 94/21807 (Inglis et al: Cantab Pharmaceuticals Research Ltd). and WO 94/03207 (D Knipe: Harvard) (all hereby incorporated by reference). Suitable examples of such genes are genes for essential viral glycoproteins, e.g. (late) essential viral glycoproteins such as gH, gL, gD, and/or gB, and other essential genes. Essential genes of human herpesviruses are identifiable from D J McGeoch, 'The Genomes of the Human Herpesviruses', in Ann Rev Microbiol 43 (1989) pp 235–265, and references cited therein. Reference is also made to data for homologues of gH glycoprotein in for example EBV, CMV and VZV, published e.g. in Desai et al, J Gen Virol 69 (1988) 1147). Mutant viruses in which such genes have been deleted or otherwise inactivated are unable to produce infectious new viral particles as progeny when they infect normal host cells, i.e. cells other than cells of host cell lines which have been made recombinant so as to express a gene corresponding to what has been inactivated in the mutant virus. Sometimes, as for example with genetically gH-deleted HSV, non-infectious viral progeny particles can be produced from normal host cells. But such mutant viruses can produce infectious new viral particles as progeny when they infect host cells of the corresponding recombinant host cell line, and in corresponding processes according to the invention the mutant viruses are grown for production purposes on such recombinant host cells.

An example of the invention and of the further mutation, being an inactivating mutation in at least one essential viral gene, is provided by a mutant herpesvirus in which the gH gene has been deleted or otherwise inactivated in connection with this invention. The gH protein, encoded by the gH gene, is an essential viral glycoprotein normally present on the surface of a herpesvirus envelope, and thought to be involved in the process of membrane fusion during entry of a herpesvirus as it infects a cell.

The deletion of gH or other essential gene can also provide an insertion site for the coding sequences for one or more polypeptides. Thus the mutant virus genome can further comprise a DNA insert encoding a heterologous polypeptide expressible within a cell infected by the mutant virus.

Thus the genome of the present mutant virus has at least two mutations, so that the mutant has a reduced ability to cause a cell that it infects to enter a productive lytic cycle, but even if a cell infected by the virus does enter a productive lytic cycle, no infectious new virus particles are produced as progeny.

The present mutant virus can be grown on a complementing cell line, i.e. a cell line derived from a parent cell of a type on which the parent wild-type herpesvirus can grow, but on which the mutant virus will not grow; the complementing cell line has been made recombinant by insertion of DNA encoding a product that complements the inactivating mutation (b) mentioned above in an essential viral gene, so that the mutant virus will grow on it (see for example specifications WO 92105263 and WO 94121807 (Inglis et al: Cantab Pharmaceuticals Research Limited)). In certain cases it can be convenient to make the complementing cell line complement both of the mutations (a) and (b). Thus, in the case where mutation (a), which reduces the ability of the mutant virus to enter the productive lytic cycle in an infected cell or cause lysis of an infected cell, is for example an inactivating mutation in gene IE0, or in another IE gene which is either essential or nearly essential for growth and production of infectious new virus particles such as IE4 or IE27, then it can be convenient to grow the mutant virus on a cell line that not only complements mutation (b), by expressing a gene product corresponding in function to the gene product of the gene affected by mutation (b), but also complements mutation (a), e.g. by expressing a gene product corresponding in function to the gene product of the gene affected by mutation (a). For example, in the case of a mutant herpes simplex virus according to an example of the invention that is a deletant in respect of gene IEO, and also a deletant in respect of gene gH, a useful corresponding cell line can for example be a recombinant Vero cell line that has been made recombinant and able to express both the gH gene and the IEO gene. As an alternative a cell of an appropriately transgenic animal or bird as described in WO 95103399 (Inglis et al: Cantab Pharmaceuticals Research Limited) can be used. It is preferred, however, not to complement a mutation in the VP16 gene in the complementing cell line, since the effect of the mutation in this particular gene is considered to be obtained where the mutant gene product forms part of the virion. It can be seen that the mutant virus as grown on the complementing cell line is free of admixture with virus that is replication-competent in normal host cells.

The nature of the mutation(s) created in the target essential viral gene(s) is a matter of choice. Any change which produces a non-functional gene product can be satisfactory, preferably being such as to minimise risk of reversion to a wild type structure. Such changes include interruption of the target with extraneous sequences and creation of specific deletions. The preferred mutation for a virus intended for use in treatment of humans however is a deletion that encompasses the entire sequence to be introduced into the complementing cell. This approach minimises the risk of regenerating wild type virus through recombination between the virus and cell DNA in the complementing cell.

A particular example of a mutant virus according to the invention. more particularly described below, is based on HSV-1 and includes the. mutation of mutant strain in1814 and complete deletion of the glycoprotein gH gene. It is considered that since the mutation in 1814 is a small sequence Insertion. there is an appreciably high probability that the mutant will revert to wild-type in respect of its VP16 function. Thus with strain in1814 there is a finite probability of lytic infection developing and this probability varies from cell type to cell type. The mutant virus example described below has the safety advantage over strain in1814 of a much reduced or zero risk of reversion to replication competence and lytic ability.

Thus mutant virus provided by the invention can be used as a vector suitable for e.g. gene therapy, and possessing a reduced ability to enter the productive lytic cycle which normally would release viral progeny from the cell. This can in particular be achieved where the vector has a reduced ability to express the Immediate-early genes (or α-genes) which are required for transcription of the early and late genes of the productive cycle.

As mentioned earlier, HSV is considered to have potential as a vector as its genome is large enough to accommodate considerable additional genetic information. Several examples of recombinant HSV viruses carrying and expressing foreign genetic material have already been described (e.g. M W Ligas and D C Johnson, J Virol 62(5) 1988 pp 1486–1494, as well as specification WO 92/05263 cited above). Thus a virus based upon a herpes virus (such as HSV) with a defect in an essential virus gene as described above, and a modification of a gene which reduces the ability to cause cell lysis, provides a particularly safe vector for use as a vaccine or for gene therapy. In the event of recombination leading to reversion of the mutation of the gene which reduces the ability to cause cell lysis (i.e. making the virus functionally of wild type in relation to this gene) the virus would regain have the ability to go into a productive lytic cycle, but if this happened, then the outcome would be the production of non-infectious virus particles which cannot infect further cells.

It may not be necessary to have or use an insertion site, if the mutant herpes virus is intended for raising an immune response against antigens coded by the virus itself, instead of against antigens coded for by sequences heterologous to the virus.

Alternatively, the genome of a mutant virus of the invention can comprise coding sequences encoding one or more polypeptides against which it is desirable to raise an immune response.

A further embodiment of the invention provides a recombinant herpesvirus vector carrying (a) a mutation that reduces the capability of the virus to cause lysis of a cell that it infects, (b) an inactivating mutation in an essential viral gene and (c) a gene intended to be expressed in a host cell infected by the vector. said gene being inserted at the site of the essential viral gene affected by the inactivating mutation (b).

Thus the invention also provides a mutant herpesvirus with a genome which includes a coding sequence(s) for one or more polypeptides, in which the coding sequence(s) can comprise gene(s) for gene therapy in order to supplement a patient with a protein normally absent or functionally defective in the patient.

Techniques for the insertion of heterologous DNA into such a viral mutant at the site of an inactivating mutation in an essential gene are known and described for example in specifications WO 92/05263 (Immunology Ltd) and WO 94/21807 (Cantab Pharmaceuticals Research Ltd). Such techniques can be readily adapted for the insertion of other genes. e.g. genes known for incorporation into other vectors intended for use in gene-therapy treatment of corresponding disease. Suitable examples of other such genes include: the gene for human adenosine deaminase (ADA), as mentioned in for example WO 92/10564 (K W Culver et al: US Secretary for Commerce & Cellco Inc), WO 89/12109 & EP 0 420 911 (I H Pastan et al); the cystic fibrosis gene and variants described in WO 91/02796 (L-C Tsui et al: HSC Research & University of Michigan), in WO 92/05273 (F S Collins & J M Wilson: University of Michigan) and in WO 94/12649 (R J Gregory et al: Genzyme Corp); or a gene for tyrosine hydroxylase.

Further, a mutant virus as provided by the present application can be used in another way, as an immunogen or vaccine, to introduce into a patient a sequence coding for a polypeptide against which it is desirable to raise an immune response. either against viral antigens, or where the mutant is used as a vector, against the encoded polypeptide(s) heterologous to the virus.

The present invention also provides a method of manufacturing (propagating) such a mutant virus which comprises culturing cells infected with the mutant virus, the cells also expressing a gene which complements the defective gene essential for the production of infectious virus, so as to allow the production of infectious virus particles containing the defective genome. and recovering the mutant virus from the culture.

The mutant virus vectors can be used according to the invention for the delivery to cells of nucleotide sequence(s) encoding polypeptidets), e.g. the ADA or other gene products mentioned above. For that purpose the virus vectors can be formulated into pharmaceutical formulations which can comprises ancillary ingredients corresponding to the formulation of conventional live virus vaccines. They can be dosed to treated subjects either in single doses or in multiple doses spaced by intervals for example of from about a week to about 4–8 weeks or more, and at doses for example at the rate of from about $10^3$ through $10^5$ pfu up to about $10^7$ or $10^8$ pfu.

The invention also relates to cells infected by such mutant viruses, e.g. to cells of the haematopoietic system such as lymphocytes, which can be infected if desired ex vivo, optionally for reinfusion into a subject from whom such cells were obtained before their infection.

Further aspects of the invention will be apparent from the following description.

DESCRIPTION OF PARTICULAR EMBODIMENT(s)

To illustrate further the present invention and how to carry it out, a preferred embodiment is described below, with reference to accompanying drawings, given by way of example only and not by way of limitation.

All genetic manipulation procedures mentioned herein are carried out according to standard methods described in 'Molecular Cloning, A Laboratory Manual', eds. Sambrook, Fritsch and Maniatis, Cold Spring Harbor Laboratory Press. 1989, incorporated by reference. The example below refers to the construction and properties of a gH-defective virus as described in WO 92/05263 and in A Forrester et al, J Virol 66(1), 1992, pp 341–348.

The virus construct described in WO 92/05263 and in A Forrester et al, J Virol 66(1) 1992, pp 341–348, contains a deletion of part only of the gH gene, and the complementing cell line described therein contains the entire gH gene plus some flanking sequences. This system of mutant virus and recombinant complementing cell line is not free of a small risk of reversion to generate gH+ virus by homologous recombination of the gH− virus with sequence in the complementing cell line. As recommended in WO 92/05263 a further cell line has also been derived which contains only the gH gene (ie without the flanking sequences from the virus). Further, a plasmid has been constructed which. if recombined into the HSV-1 genome, removes the entire gH gene. In the result there is no homology between the sequences inserted into the cell line and viral sequences, and there the small risk of homologous recombination to generate replication-competent gH+ virus is removed.

The accompanying details describe inter alia:

1. The construction of a cell line (CR1) which contains the HSV-1 gene, but no flanking sequences.

2. The construction of plasmid pIMMB27+ which contains sequences flanking gH and a LacZ expression cassette replacing, precisely, gH coding sequences.

3. The construction of a virus (HSV-1 in1814) containing the in1814 mutation and lacking gH, by co-transfection of cells with in1814 DNA and plasmid pIMMB27+.

MATERIALS AND METHODS

Construction of a Type I gH Expression Cell Line

A cell line able to express gH is used to generate and grow up gH deletion mutant virus. An example of such a cell line is described in specification WO 92/05263. An alternative and now preferred method of construction of such a cell line is as follows.

Plasmids

Construction of plasmids used for generation of type I gH expression cell line and type I QH deletion mutant pIMMB25

Figure 1:
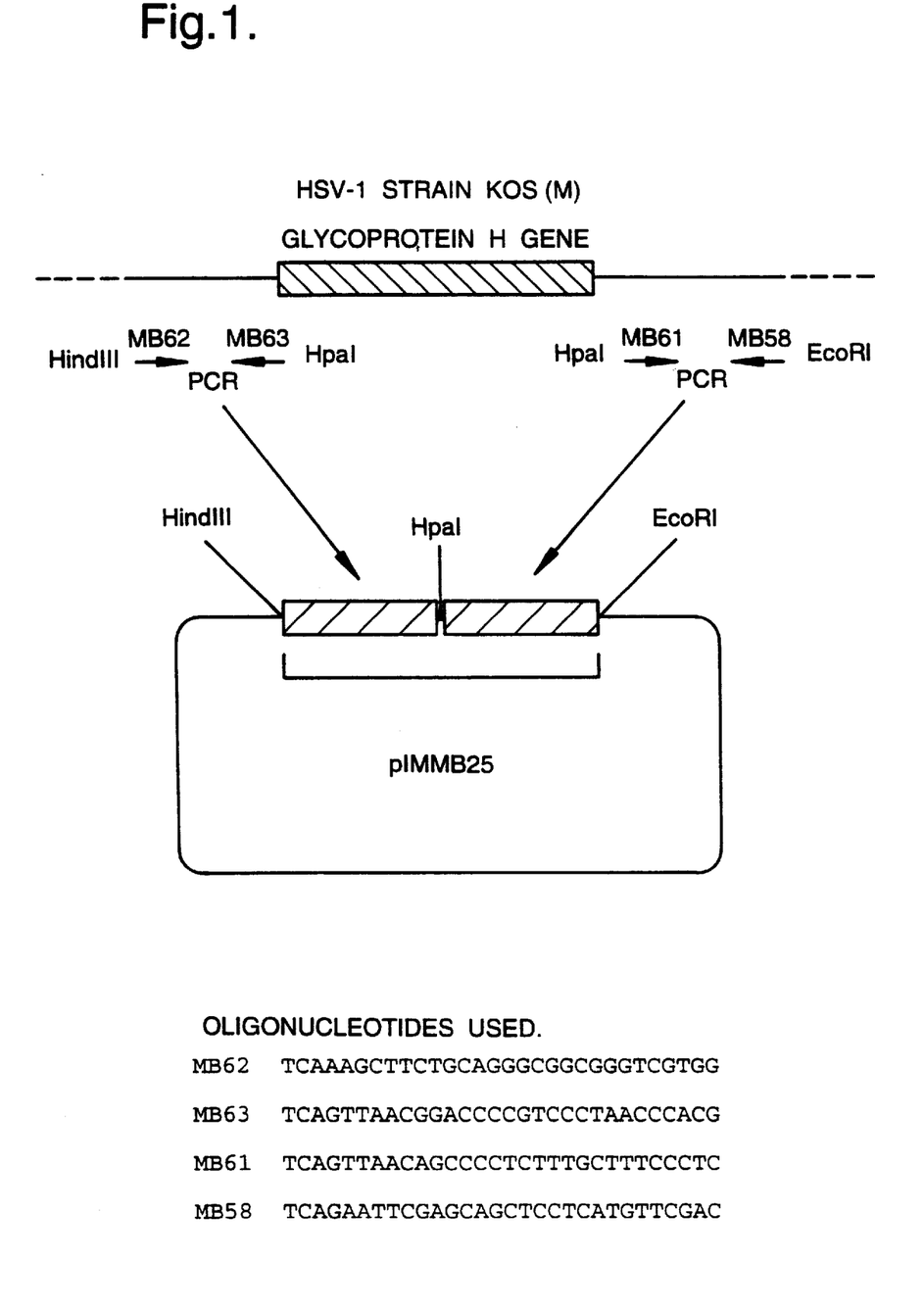
FIG. 1 shows the construction of a plasmid pIMMB25.

Flanking sequences to either side of the gH gene are amplified from HSV-1 strain KOS(m) viral DNA by the polymerase chain reaction (PCR) using Vent DNA polymerase (New England Biolabs) which has a lower error rate than Taq DNA polymerase. FIG. 1 shows the regions cloned by PCR, and the oligonucleotides used. The fragment amplified with oligonucleotides MB62 (TCAAAGCTTCTGCAGGGCGGCGGGTCGTGG) (SEQ. ID. No. 1) and MB63 (TCAGTTMCGGACCCCGTCCCTMCCCACG) (SEQ. ID. No. 2) (FIG. 1) is digested with EcoRI and HpaI, and the fragment amplified with oligonucleotides MB61 (TCAGTTMCAGCCCCTCUTGCTTTCCCTC) (SEQ. ID. No. 3) and MB58 (TCAGMTTCGAGCAGCTCCTCATGTTCGAC) (SEQ. ID. No. 4) (FIG. 1) is digested with HpaI and HindIII. These fragments are gel-purified and cloned into EcoRI-HindIII-cut pUC119. The resultant plasmid is designated pIMMB25.

pIMMB27+

Figure 2:
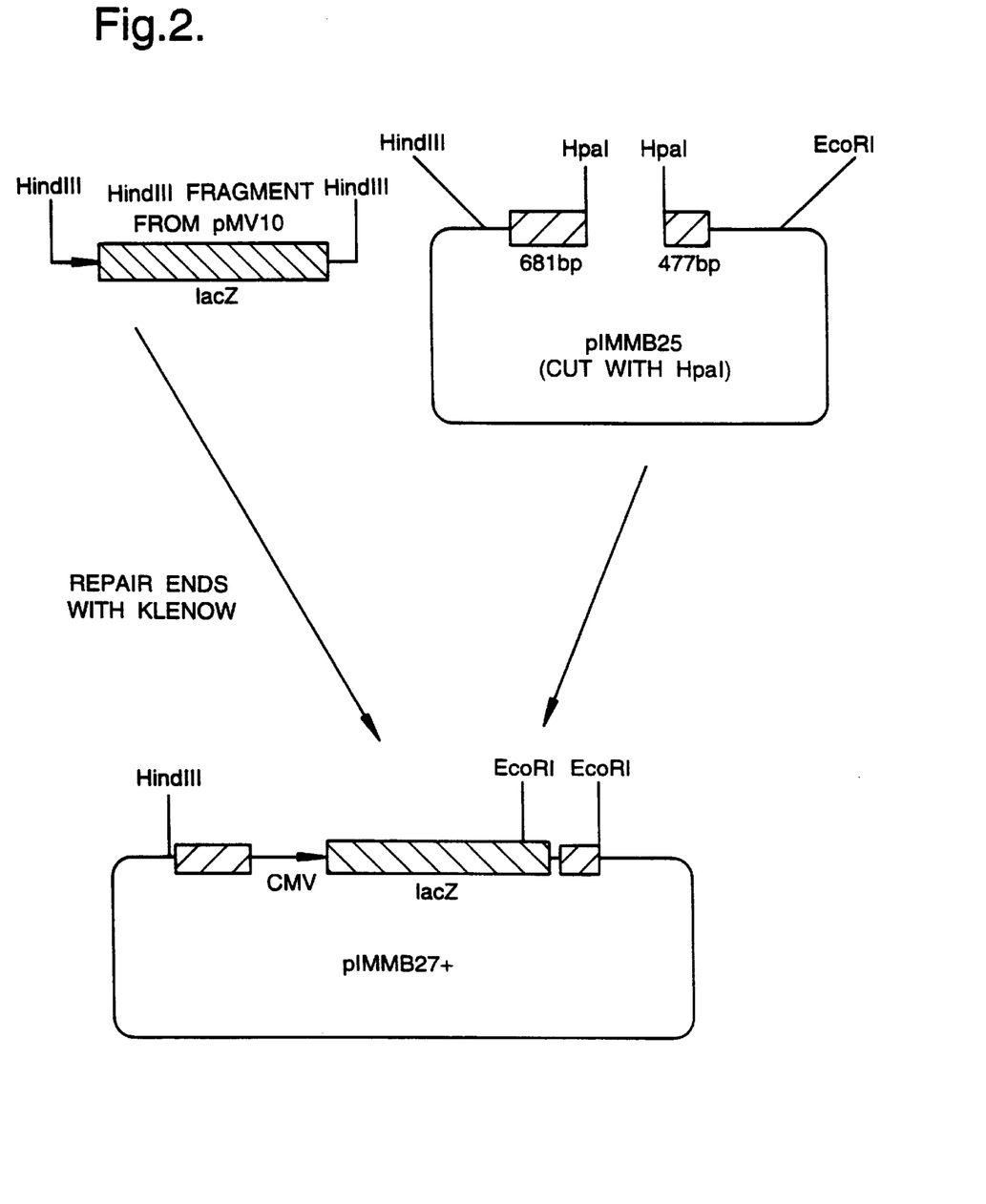
FIG. 2 shows the construction of a plasmid pIMMB27+.

A CMV-lacZ cassette is excised from the vector pMV10 by digestion with HindIII.(see A Forrester et al, J Virol 66 (1992), pp 341–348; Wilkinson & Akrigg, Nucleic Acids Research, 20, 1992, p 2233). Alternatively pCH110 from Pharmacia P-L Biochemicals Inc., Milwaukee Wis., USA can be used, in which case the SV40 promoter with lacZ gene can first be excised using appropriate restriction enzymes. The fragment is made blunt-ended by repair with Klenow polymerase and then gel-purified. The purified fragment is cloned into the HpaI site of pIMMB25. A clone in which the CMV-lacZ cassette is inserted in the same orientation as the gH gene is selected. This plasmid is designated pIMMB27+(see FIG. 2).

pIMC05

Figure 3:
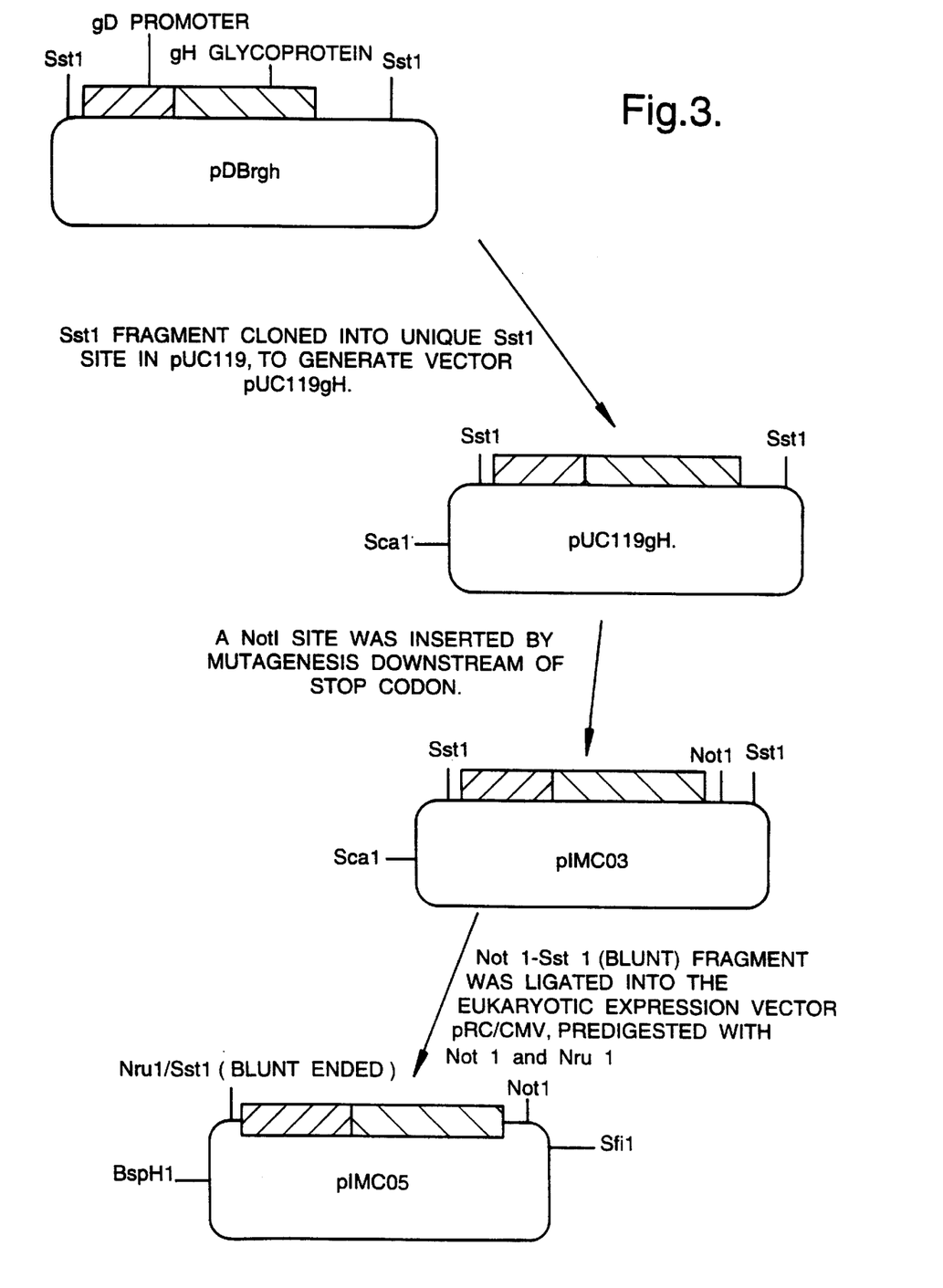
FIG. 3 shows the construction of a plasmid pIMC05.

A plasmid pIMC05 can then be constructed as follows: A 4.3 kb Sst-I fragment encoding the HSV-1 (HFEM) gH gene and upstream HSV-1 gD promoter (−392 to +11) is excised from the plasmid pgDBrgH (see A Forrester et al., J. Virol. 66, 1992, 341–348) and cloned into vector pUC119 (J Vieira and J Messing, Methods in Enzymology 153 (1987) 3–11) to produce plasmid pUC119gH. A NotI site is introduced into plasmid pUC119gH by site-directed mutagenesis, 87 bp downstream of the stop codon. The resulting plasmid, pIMC03, is used to generate a NotI-SstI (blunt) fragment which is repaired and ligated into the eukaryotic expression vector pRC/CMV (Invitrogen Corporation/R&D Systems, UK). predigested with NotI and NruI to remove the CMV IE promoter. The resulting plasmid is designated pIMC05 and contains the HSV-1 gH gene under the transcriptional control of the virus inducible gD promoter and BGH (bovine growth hormone) poly A. It also contains the neomycin resistance gene for selection of G418 resistant stable cell lines (see FIG. 3).

Cells Capable of Expressing Type I gH

The plasmid pIMCO5, constructed in the manner described above as a gH-expressing vector (HSV-1 gH), is transfected into Vero cells (ATCC no. 88020401) using the calcium phosphate technique (Sambrook. Fritsch & Maniatis, A Laboratory Manual, Cold Spring Harbor Laboratory Press). Cells are selected by dilution cloning in the presence of G418 and a clonal cell line is isolated. Following expansion and freezing, cells were seeded into 24 well plates and tested for their ability to support the growth of gH-negative virus, by infection with SC16ΔgH (A Forrester et al, J Virol 66, 1992, pp 341–348) at 0.1 pfu/cell. Virus plaques can be observed 3 days post infection confirming expression of the gH gene. A suitable example of a gH-expressing cell line which supported the growth of SC16ΔgH was isolated in this way, and was designated CR1.

Construction of Recombinant Virus (HSV-1 gH-negative in1814)

The HSV-1 mutant virus in1814 (C I Ace et al, J Virol 63, 1989, pp 2260–2269; C I Ace et al, J Gen Virol 69, 1988, p 2595; R A Harris and C M Preston, J Gen Virol 72, 1991, p 907) is grown in the presence of hexamethylene bisacetamide (HMBA) to overcome the defect in the VP16 gene. Deletion of the glycoprotein H gene is performed on the background of this virus mutant (in1814) so that the resulting virus is both gH– deleted and defective in VP16.

Transfection on F6 cells (see A Forrester et al, J Virol, 66, 1992, pp 341–348) which express the gH gene of HSV-1 can be performed by the modified calcium phosphate procedure of Chen and Okayama (Chen & Okayama, Mol Cell Biol 7, 1987, 2745). Cells are transfected with 20 μg of HSV-1 (in1814) infected-cell DNA plus 5 μg of plasmid pIMMB27+.

Recombination events occur. involving flanking sequences in plasmid pIMMB27+and homologous sequences in HSV-1 (in1814) DNA, leading to replacement of the gH gene by the CMV-lacZ cassette.

After three days, the cells which exhibit extensive cytopathic effect are harvested and sonicated. Dilutions of transfection progeny are plated on F6 cells, and after 3 days, recombinant plaques are detected by using an overlay of 1% low-melting-temperature agarose containing X-gal (300 μg/ml). Blue plaques are picked and subjected to two further rounds of plating and plaque picking. A single plaque can be picked and stocks subsequently grown in CR1 cells to eliminate the possibility of gH rescue by recombination.

In an alternative procedure, recombinant virus can for example be constructed by transfection of mutant in1814 viral DNA with the plasmid pIMMB27, using the following adaptation of standard transfection procedure. Viral DNA is purified on a sodium iodide gradient as described in Walboomers & Ter Schegget (1976, Virology 74, 256–258). Recombination is carried out as follows: A transfection mix is prepared by mixing 5 micro-g of viral DNA, 0.5 micro-g of linearised plasmid DNA (linearised by digestion with the restriction enzyme ScaI) in 1 ml of HEBS buffer (137 mM NaCl, 5 mM KCl. 0.7 mM $Na_2HPO_4$, 5.5 mM glucose. 20 mM Hepes, pH 7.05). 70 micro-l of 2M $CaCl_2$ is added dropwise, and mixed gently. The medium is removed from a sub-confluent 5 cm dish of complementing cells (e.g. CR1 cells as decribed above) able to express type I gH, and 500 micro-l of the transfection mix is added to each of two dishes. The cells are incubated at 37 deg.C for 40 minutes, when 4ml of growth medium containing 5% foetal calf serum (FCS) are added. 4 hours after adding the transfection mix, the medium is removed and the cells washed with serum-free medium. The cells are then 'shocked' with 500 micro-l per dish of 15% glycerol for 2 minutes. The glycerol is removed, the cells are washed twice with serum-free medium and growth medium containing 5% FCS is added.

After 4–7 days, when a full viral cytopathic effect (CPE) is observed, the cells are scraped into the medium, spun down at 2500 rpm for 5 minutes at 4 deg C. and resuspended in 120 micro-l of Eagles minimal essential medium (EMEM). This is now a crude virus stock containing wild-type and recombinant virus. The stock is frozen, thawed and sonicated and screened for recombinants on complementing cells expressing type I gH at a range of dilutions. After addition of the virus dilutions, the cells are overlaid with medium containing 1% low-gelling temperature agarose. After the appearance of viral plaques at about 3 days, a second overlay of agarose containing 330 micro-g/ml of Xgal is added. Blue plaques are picked, within 48 hours, and transferred to 24-well dishes (1 sq cm per well) containing complementing cells expressing type I gH. The plaques are allowed to grow to full CPE and harvested by scraping into the medium. Multiple rounds of plaque-purification are carried out until a pure stock of virus is obtained.

The structure of the recombinant in the region of the gH locus can be confirmed as follows. Sodium iodide purified viral DNA is prepared as before, and digested with BamHI. This digest is separated on an agarose gel and transferred to a nylon membrane. This can be probed with a radiolabelled DNA fragment homologous to the sequences either side of the gH gene.

(In alternative but less preferred methods for generating generally similar mutant viruses, the deletion of the essential viral gene, e.g. the glycoprotein gH gene, can be carried out before creating the defect in the VP16 gene.)

Effects of gH-negative in1814 mitant HSV-1 in vivo

Groups of 10 mice were infected with $2 \times 10^7$ pfu of in1814 gH– virus (derived by the method described above). directly into the sciatic nerve. After 60 days, the animals were sacrificed and the spinal ganglia removed. The presence of latent viral genomes was assessed by in situ hybridization to detect latency associated transcripts. Positive neurones were detected at the frequency of 0.27/ganglionic section, this showing the establishment of latency in vivo.

Test of replication-incompetence of gH-negative in1814 mutant HSV-1

A dose of $3.7 \times 10^8$ pfu of virus derived by the method described above (approximately 10 times the dose of virus used in the in-vivo experiment described above) was used to infect $10^9$ BHK cells in culture. No viral plaques were observed in the culture after 3 days. This indicates a very high level of safety in the in1814 gH-negative mutant combination against the risk of reversion to replication-competence.

Construction and Use of Vectors Containing Inserted Heterologous DNA

The construction of a vector corresponding to the in1814 gH– negative HSV1 described above can be achieved for example by inserting a gene of interest, under control of a CMV IE promoter or HSV gD promoter, either in place of the lacz cassette mentioned above, or in series with the lacz cassette.

The mutant viruses and vectors described herein can be formulated as pharmaceutical formulations in any of the ways conventionally used for the formulation of live virus vaccines. The vectors can be given in single or multiple doses at the rate of from about $10^3$ through $10^5$ pfu up to $10^7$ or $10^8$ pfu. Pfu can be estimated in the case of the example vector obtained as described above, by culture on CR1 or F6 cells in the presence of HMBA.

The invention described herein is susceptible of modifications and variations that will be apparent to the reader of ordinary skill in the field, and the above disclosure extends also to combinations and subcombinations of the features mentioned or described herein and in the cited publications, which are hereby incorporated by reference.

What is claimed is:

1. A mutant herpesvirus comprising (a) a first mutation such that the virus has a reduced ability in comparison with a parent type to cause lysis of an infected cell, and (b) a second inactivating mutation in an endogenous gene which is essential for the production of infectious virus but is not essential for viral DNA replication,
wherein the mutation (a) is a mutation effective to reduce the ability of the virus to cause expression of at least one immediate early gene function.

2. A mutant herpesvirus according to claim 1, wherein mutation (a) is a mutation in the VP16 gene which is effective to reduce the transinducing properties of the protein encoded by that gene.

3. A mutant herpesvirus according to claim 2, wherein mutation (a) is a mutation in the VP16 gene that allows growth of the mutant virus in cell culture in the presence of hexamethylene bisacetamide (HMBA).

4. A mutant herpesvirus according to the claim 2, wherein mutation (a) is a mutation in an immediate early gene.

5. A mutant herpesvirus according to claim 1, wherein mutation (a) is a mutation in a member of the group consisting of ICP0, ICP4, ICP22 and ICP27.

6. A mutant herpesvirus comprising (a) a first mutation such that the virus has a reduced ability in comparison with a parent type to cause lysis of an infected cell, and (b) a second inactivating mutation in an endogenous gene which is essential for the production of infectious virus but is not essential for viral DNA replication, wherein the herpesvirus is a herpes simplex virus of type 1 (HSV-1) or a herpes simplex virus of type 2 (HSV-2) and wherein mutation (a) is a mutation in a gene encoding ICP0.

7. A mutant herpesvirus comprising (a) a first mutation such that the virus has a reduced ability in comparison with a parent type to cause lysis of an infected cell, and (b) a second inactivating mutation in an endogenous gene which is essential for the production of infectious virus but is not essential for viral DNA replication, wherein the herpesvirus is a herpes simplex virus of type 1 (HSV-1) or a herpes simplex virus of type 2 (HSV-2) and wherein mutation (a) is a mutation in a gene encoding ICP4.

8. A mutant herpesvirus comprising (a) a first mutation such that the virus has a reduced ability in comparison with a parent type to cause lysis of an infected cell, and (b) a second inactivating mutation in an endogenous gene which is essential for the production of infectious virus but is not essential for viral DNA replication, wherein the herpesvirus is a herpes simplex virus of type 1 (HSV-1) or a herpes simplex virus of type 2 (HSV-2) and wherein mutation (a) is a mutation in a gene encoding ICP22.

9. A mutant herpesvirus comprising (a) a first mutation such that the virus has a reduced ability in comparison with a parent type to cause lysis of an infected cell, and (b) a second inactivating mutation in an endogenous gene which is essential for the production of infectious virus but is not essential for viral DNA replication, wherein the herpesvirus is a herpes simplex virus of type 1 (HSV-1) or a herpes simplex virus of type 2 (HSV-2) and wherein mutation (a) is a mutation in a gene encoding ICP27.

* * * * *